US00PP13966P39

(12) United States Plant Patent
Lighty

(10) Patent No.: US PP13,966 P3
(45) Date of Patent: Jul. 8, 2003

(54) *EPIMEDIUM GRANDIFLORUM* PLANT NAMED 'PURPLE PIXIE'

(75) Inventor: Richard W. Lighty, Kenneth Square, PA (US)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/871,733

(22) Filed: Jun. 4, 2001

(65) Prior Publication Data

US 2002/0194660 P1 Dec. 19, 2002

(51) Int. Cl.[7] ..... A01H 5/00
(52) U.S. Cl. ..... Plt./263
(58) Field of Search ..... Plt./263

(56) References Cited

PUBLICATIONS

The RHS Dictionary of Gardening, vol. 2, The Stockton Press, New York, New York, 1992, p. 174.*

Epimedium cultivars, Dr. Leonard Perry, http://pss.uvm.edu/pss123/perepmid.html, Aug. 18, 2002.*

Epimedium 'Lilafee', http://www.pernellgerver.com/epimedium.htm, Horticultural Communication Services, 1999–2002.*

* cited by examiner

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

A new variety of *Epimedium grandiflorum* is provided that is well suited for growing as a distinctive ground cover. The new variety flowers in May and forms attractive deep purple blossoms with white spurs that commonly are borne above the foliage. The young foliage is violet-colored and the mature foliage is olive green with maroon margins. During observations to date the new variety has been found to be more amenable to expeditious asexual propagation by division than other commonly grown varieties of the species. The available choices in ornamental ground covers are expanded.

1 Drawing Sheet

Botanical / commercial classification: *Epimedium grandiflorum* / Bishop's Hat.
Varietal denomination: cv. 'Purple Pixie'.

SUMMARY OF THE INVENTION

The new *Epimedium grandiflorum* variety of the present invention was observed during the late 1970's as a found seedling in the garden of my home at Kennett Square, Pa., U.S.A. The exact parentage of the new variety is unknown. Other *Epimedium grandiflorum* varieties growing nearby included 'White Queen' (non-patented in the United States) and 'Rose Queen' (non-patented in the United States). It is considered likely that the 'White Queen' variety was the female parent and the 'Rose Queen' variety was the male parent. Such presumed parentage of the new variety of the present invention can be expressed as follows:

'White Queen'×'Rose Queen'.

The new variety of the present invention was carefully preserved and further observed and studied for a number of years. The final selection of the new variety of the present invention occurred in 1994. Had the new variety of the present invention not been discovered and preserved it would have been lost to mankind.

If was found that the new variety of the present invention exhibits the following combination of characteristics:

(a) forms attractive deep violet flowers with white spurs that commonly are borne above the foliage, (b) forms violet-colored young foliage and olive green mature foliage with maroon margins, and (c) is particularly well suited for growing as a distinctive ornamental ground cover.

The new variety of the present invention readily can be distinguished from the 'White Queen' variety by the presence of deep violet flowers and violet coloration on the new foliage. The 'White Queen' variety forms white flowers and lacks the violet coloration on young foliage.

The new variety of the present invention readily can be distinguished from the 'Rose Queen' variety by the formation of deep violet flowers instead of the rose-colored flowers of 'Rose Queen' variety.

The new variety of the present invention readily can be distinguished from the 'Lilafee' variety (non-patented in the United States) through the display of a larger growth habit, a darker deep violet flower coloration, and a propensity to form a more noticeable second flush of growth that tends to cover and conceal older flower stalks from the first flush of blooms. The second flush of growth by the new variety of the present invention is accompanied by additional sporadic blooms which typically are absent in the 'Lilafee' variety. However, this additional bloom formation in the new variety tends to decrease somewhat as the plants get older.

The new variety of the present invention well meets the needs of the horticultural industry and expands the choices of herbaceous perennials, and especially the ornamental ground covers. It performs well in rock gardens and as a border planting. The attractive flowers usually are held well above the foliage and commonly are formed in May at Eastern, Pa., U.S.A.

Division has been used to asexually propagate the new variety at Kennett Square and West Grove, Pa., U.S.A. It has been found that the distinctive combination of characteristics of the new variety is firmly fixed and is reliably transmitted to succeeding generations following such division. During observations to date the new variety has been found to be more amenable to expeditious asexual propagation by division than other commonly grown varieties of the species.

The new variety has been named 'Purple Pixie'.

BRIEF DESCRIPTION OF THE PHOTOGRAPHS

The accompanying photographs show specimens of the new variety in color as nearly true as it is reasonably possible to make the same in color illustrations of this nature. The plants were approximately two years of age and were being grown during the summer on their own roots at West Grove, Pa., U.S.A.

DETAILED DESCRIPTION

Figure 1:
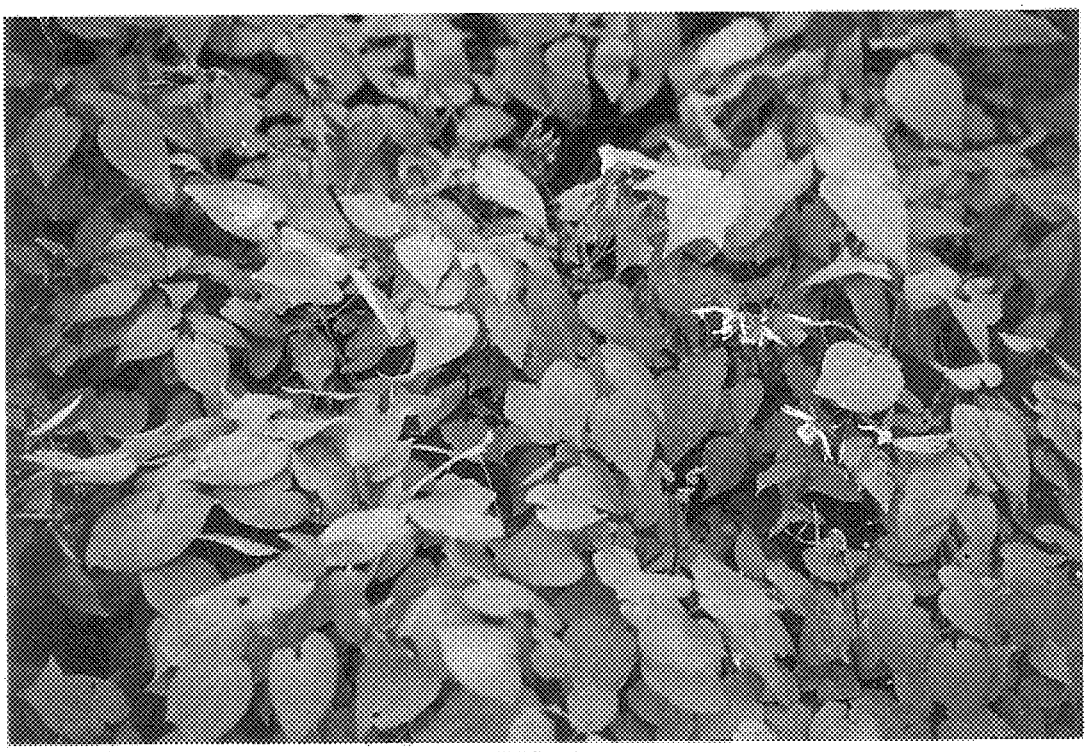
FIG. 1 illustrates the olive green foliage with maroon margins of the new variety of the present invention. Violet-colored young foliage also is shown.

The following is a detailed description of the new variety that was obtained while observing plants being grown outdoors at West Grove, Pa., U.S.A., during May. The plants were approximately two years of age and were being grown on their own roots. The chart used in the identification color is The R.H.S. Colour Chart of The Royal Horticultural Society, London, England. More common color terms are to be accorded their ordinary dictionary significance.

Botanical classification: *Epimedium grandiflorum*, cv. 'Purple Pixie'.

Plant:

*Habit.*—Vigorous.

*Type.*—Biternate, deciduous.

*Height.*—Approximately 30 to 45 cm.

*Width.*—Approximately 60 to 75 cm.

*General appearance.*—Tight slowly-spreading clump of plant growth.

*Rhizomes.*—Short, irregularly branched and commonly present within approximately 3 cm of the surface of the ground. The larger primary rhizomes typically display a length of approximately 10 to 15 mm during the first year of growth including a large terminal bud having a length of approximately 5 to 10 mm. Such primary rhizomes commonly have a diameter of approximately 7 to 8 mm with the terminal buds displaying the same diameter or slightly less. The production of a leaf or inflorescence terminates the growth of the rhizome tip. One or two axillary buds located basipitally commonly develop into rhizomes that grow for one or two years and then develop into a terminal leaf or inflorescence. This branching causes the formation of a dense mat of rhizomes. In some instances a rhizome may only elongate for a year and not produce an aerial stem though it will still branch. The typical internode length on the rhizomes is approximately 1 to 2 mm.

Leaflets:

*Shape.*—Cordate.

*Length.*—Approximately 3 to 5 cm.

*Width.*—Approximately 2 to 3 cm.

*Margins.*—Serrate with spiny teeth-like appendages.

*Apex.*—Acuminate.

*Base.*—Cordate.

*Texture.*—Smooth and satiny on young foliage, and somewhat rough and leathery on mature foliage.

*Venation.*—Palmate.

Figure 2:
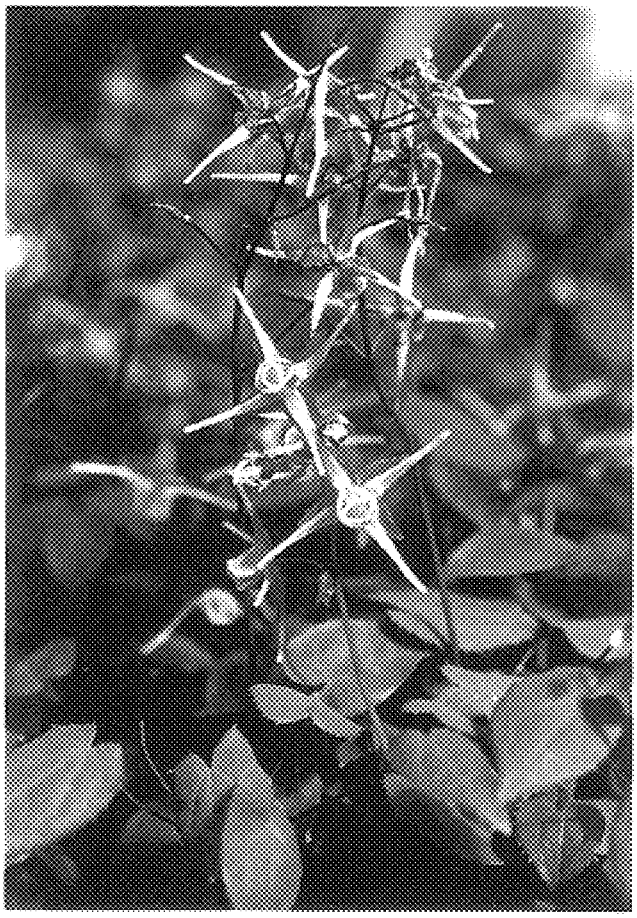
FIG. 2 illustrates the deep violet flowers with white spurs as they commonly are displayed well above the foliage. The maroon margins of the olive green mature foliage also are shown.

*Color.*—Young Foliage: On the dorsal side a combination of Greyed-Purple Group 183B and Greyed-Orange Group 166A changing to violet as shown in FIG. 1, and on the ventral side Grey Group 201A. The venation is Green Group 142A. Adult Foliage: On the dorsal side Yellow-Green Group 144A and 144B, and on the ventral side Green Group 139C and 139D. The leaflets possess maroon margins as shown in FIG. 2. This maroon coloration is believed to be most pronounced and observable in early summer when the foliage newly matures. The venation is Yellow-Green Group 149D.

*Petiole.*—Commonly approximately 2 to 3 cm in length.

*Stem color.*—Greyed-Green Group 195B with a cast of Greyed-Orange Group 177D.

Inflorescence:

*Type.*—Raceme.

*Flowering time.*—May.

*Flower make up.*—Four outer sepals, four inner sepals, and four petals with spur appendages located at the ends/tips of the petals. The outer sepals tend to drop when the flower completely opens.

*Corolla.*—With long hollow nectariferous backward projecting spurs of the petals.

*Size.*—Symmetrical and approximately 3.5 cm from tip of spur to tip of spur.

*Number.*—Approximately 5 to 7 flowers per raceme.

*Stamens.*—Five.

*Pistil.*—One.

*Fragrance.*—None.

*Color.*—Outer Sepals: The dorsal surface ranges from Greyed-Purple Group 186B to 186C, and the ventral surface is Greyed-Purple Group 187B with Greyed-Purple Group 186B on the edges. Inner Sepals: The dorsal surface is Red-Purple Group 71A, and the ventral surface is Red-Purple Group 72B to 72C. Petals: The dorsal surface is Purple Group 76B, 76C, and 76D, and the ventral surface is Purple Group 76C and 76D. Spurs: White Group 155A. Stamens: A combination of Yellow-Green Group 151C and 153D. Pistil: Green Group 143B. Fertility: No firm basis is known to conclude that the plant is infertile; however, no fruit has been observed to date.

Development:

*Vegetations.*—Clump-forming.

*Blooming.*—Primarily in May and sporadically throughout the spring.

*Resistance to diseases.*—No particular susceptibility to diseases has been noted during observations to date.

Plants of the new 'Purple Pixie' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of *Epimedium grandiflorum* plant that exhibits the following combination of characteristics:

(a) forms attractive deep purple flowers with white spurs that commonly are borne above the foliage, (b) forms violet-colored young foliage and olive green mature foliage with maroon margins, and (c) is particularly well suited for growing as a distinctive ornamental ground cover;

substantially as illustrated and described.

* * * * *